United States Patent [19]

Warshaw et al.

[11] Patent Number: 4,996,046

[45] Date of Patent: Feb. 26, 1991

[54] INFRARED TREATMENT FOR PSORIASIS

[76] Inventors: Thelma G. Warshaw, 519 E. Broad St., Westfield, N.J. 07090; Jacob Horowitz, 10 Black Birch Rd., Scotch Plains, N.J. 07076

[21] Appl. No.: 440,675

[22] Filed: Nov. 24, 1989

[51] Int. Cl.$^5$ .................... A61K 31/74; A61K 7/42
[52] U.S. Cl. .................................... 424/78; 424/81; 514/844
[58] Field of Search .................. 424/78, 81; 514/563, 514/844

[56] References Cited

U.S. PATENT DOCUMENTS

| | | | |
|---|---|---|---|
| 3,575,871 | 4/1971 | Susi et al. | 524/204 |
| 3,692,688 | 9/1972 | Castellion | 524/406 |
| 4,551,490 | 11/1985 | Doyle et al. | 524/22 |
| 4,820,508 | 4/1989 | Wortzman | 514/844 |
| 4,822,600 | 4/1989 | Wortzman | 514/844 |
| 4,826,677 | 5/1989 | Mueller et al. | 428/81 |

Primary Examiner—Merrell C. Cashion, Jr.
Assistant Examiner—Peter F. Kulkosky
Attorney, Agent, or Firm—Mathews, Woodbridge & Collins

[57] ABSTRACT

Psoriasis is treated with an infrared absorbing compound, preferably but not exclusively by occluding psoriatic lesions with a plastic film containing at least one compound which strongly absorbs infrared radiation in the range of from about 700 to about 1400 nanometers. The invention also includes a dressing for treating psoriasis incorporating one or more infrared blocking compounds. The infrared absorbing materials are preferably but not necessarily dispersed uniformly through a flexible carrier transparent to visible light, such as polyvinyl chloride (PVC) film or poly (methyl methacrylate) (PMMA) film, by known techniques of solution casting or dying. The materials can be used as the sole therapeutic agent, or as an adjunct to local and/or systemic treatments for psoriasis.

6 Claims, No Drawings

INFRARED TREATMENT FOR PSORIASIS

The invention relates to the treatment of psoriasis and in particular to the use of infrared absorbing compounds in such treatment.

In treating psoriasis, a dermatosis of yet unknown origin, the use of topical creams and salves, sometimes under plastic film dressings such as kitchen-wrap films, is common.

We have discovered that conventional occlusive dressings permit the escape of substantial amounts of energy via infrared radiation through the surface layers of psoriatic lesions, and that this energy leakage aggravates the disease and tends to counteract the effectiveness of conventional treatments. Such infrared energy leakage is typically found in psoriatic lesions but is absent in healthy skin. The use of materials that prevent such leakage has been found to have distinct therapeutic benefits, producing more rapid and more pronounced relief than is provided by conventional dressings, which freely transmit infrared radiation.

Infrared radiation is defined herein as actinic radiation in the wavelength range of about 700-1400 nanometers. Human body tissues transmit these wavelengths freely; healthy skin is opaque to them; psoriatic skin is transparent to them. Conventional occlusive film dressings are transparent to them.

While not wishing to be bound by any theory, there is evidence that psoriasis is associated with a breakdown in body thermoregulation. The lesions thus characteristically occur over parts of the body prone to lose heat, such as the back of the head( the elbows and the knees. The condition, moreover, is aggravated in overweight individuals with a great deal of subcutaneous fat insulation and the condition is more prevalent in cold weather.

Non-contact thermography, i.e., measuring and recording infrared radiation, was conducted using a G.E. Spectrotherm 2000 instrument. Such measurements demonstrate that psoriasis lesions appear relatively "hot", i.e., at least 0.25° C. warmer than the surrounding uninvolved skin.

When measured by actual physical contact (using a Bailey Laboratory Thermometer, Model BAT-4), however, the psoriatic lesions are typically cooler than surrounding uninvolved skin by at least 1° C. The increased radiation but lower actual temperature at the lesion thus suggests "heat leakage".

When psoriatic lesions are covered with an occlusive dressing containing infrared absorbers and then examined by non-contact thermography, the "hot spot" phenomenon disappears, i.e., the dressing covers the lesions with the equivalent of normal infrared opaque skin. It appears a "greenhouse" environment is thereby created, which environment intensifies the healing effects of both normal physiology and topical and systemic treatments.

Infrared absorbing materials which are suitable for the embodiment of this invention, and techniques for incorporating them into plastic films suitable for occlusive dressings, are well known and disclosed for example in U.S. Pat. Nos. 3,484,467; 3,485,650; 3,557,012; 3,575,871; 3,631,147; 3,637,769; 3,692,688; 3,709,830; and 3,853,783, the disclosures of which are incorporated herein by reference. Preferred films are cellulose esters such as cellulose acetate and propionate, polyvinyl chloride, poly(methyl) methacrylate, and polycarbonates. Generally at least about 0.10% by weight of one or more infrared absorbing compounds are incorporated. Some of these materials are already present in commercial products manufactured and marketed by American Cyanamid Company and (its subsidiary, Glendale Protective Technologies, Inc., and known as PVC Laser Film ®; CyasorbR IR-99 ®; Cyasorb ® IR-126; Cyasorb ® IR-165. The present invention relates to the use of these materials and similar materials having the requisite infrared absorption spectrum and being suitable for use in dressings.

Accordingly, one object of the present invention is to provide a means for counteracting the breakdown of thermoregulation associated with psoriasis, by means of a dressing which contains infrared absorbing compounds which block the escape of body heat via infrared radiation.

Another object of the invention is to provide the well-known benefits of conventional occlusive film dressings in addition to the new and improved benefits due to infrared absorption at the site of a psoriatic lesion.

A further object of the invention is to provide convenience of use, i.e., to maximize the ease of application of the dressings, to use adhesives that stabilize the contact of dressings with skin while permitting easy removal of dressings, and to use dressings that are transparent to visible light for easy visual inspection of lesions as healing progresses.

These and other objects of the invention, which will become apparent from the following specification, have been achieved by the use of one or more infrared absorbing compounds enumerated above, constituting 0.05% to 1% or more by weight preferably dispersed in a polymeric plastic film such as PVC or PMMA. The dressing can further comprise a medical grade adhesive composition containing a polymer and a water-soluble hydrocolloid.

For the purpose of the present invention, the term dressing includes any material used to cover and protect the affected area. The dressing can be in direct contact with the affected area, partial contact, or a covering material so long as it substantially seals the affected area against the escape of infrared radiation. Additional therapeutic agents such as tar, dithranol, or corticosteroids can be placed between the dressing and the affected area. Alternatively, the dressing itself can include the medications.

The dressing can further comprise an adhesive composition, as for example, disclosed in U.S. Pat. No. 4,551,490. The adhesive comprises a polymer in combination with a water-swellable hydrocolloid such as polyisobutylene, butyl rubber, styrene radial or block copolymers, methylvinyl ether/maleic acid, isoprene, styrene butadiene, polybutene, and mixtures thereof; sodium carboxymethylcellulose, pectin, gelatin, guar gum, locust bean gum, gum karaya, and the like. Other additives useful in the adhesive composition include water-swellable cohesive strengthening agents, tackifiers, antioxidants, antipsoriatics, and/or other pharmacologically active ingredients.

Compositions which can be applied to the affected area comprise the above-described IR blocking compounds. Such a composition can be applied as a coating on the affected area, such as those disclosed in U.S. Pat. No. 4,826,677, or as a dressing applied over the affected area. As noted such compounds can further comprise any accepted antipsoriatics.

The following example is set forth herein to illustrate the nature of the invention and the manner of carrying it out. However, the invention should not be considered as being limited to the details thereof.

EXAMPLE

The clinical efficacy of IR blocking occlusive plastic dressings was tested in patients with active psoriasis in a design which compared IR blocking film (PVC Laser Film, American Cyanamid) with commercial kitchen wrap film.

Each subject was instructed to apply the IR blocking film to one active psoriasis plaque, and to apply a commercial food wrap occlusive film on a similar contralateral plaque. The dressing was secured in place for 22 hours per day, and replaced. This was repeated until there was clinical response.

In all five subjects, there was clinical improvement ranging from lesser infiltration and erythema to a complete clearing. Such improvement was greater and more rapid in every case with the IR blocking film than with the commercial plastic film. Response to IR blocking film was noted as early as eight hours, and as late as three weeks after initiation of the treatment. No detrimental side effects were observed with either kind of film dressing.

Case 1 treated sites on the lateral aspect of each leg. The IR blocking film alone induced a dramatic clearing in 48 hours as compared with minor clearing from use of commercial plastic film.

When a high potency corticosteroid was applied under the IR blocking film, a noticeable remission was observed within eight hours. The same treatment on a contralateral site with commercial plastic film did not produce such rapid response.

Case 2 applied IR blocking film on the right knee and commercial plastic film on the left knee. After one week, there was diminished scaling on the right knee as compared with the left knee.

Case 3 produced a clearing with IR blocker film application to the left arm after three weeks. The commercial film dressings produced no change in the psoriasis plaque on the contralateral site on the right arm.

Case 4 placed the occlusive IR blocker film dressings on the right thigh lateral surface. The result was paling, decreased scaling, and decreased induration ("not-bumpy like before") within 1 week. The left thigh showed only decreased scaling under commercial film dressings.

Case 5 showed reversal of enlargement of actively spreading psoriasis within 72 hours of application of IR blocking film on the right elbow and arm. A corresponding improvement on the left arm covered with commercial film dressings was not observed.

What is claimed is:

1. A method for treating psoriasis which comprises covering the affected area with a material containing an infrared absorbing amount of at least one infrared radiation blocking compound, said amount of said at least one blocking compound being sufficient to substantially reduce the escape of body heat via infrared radiation.

2. The method of claim 1 wherein the material is a dressing.

3. The method of claim 1 wherein a topical antipsoriatic medication is applied to the skin being covered film.

4. The method of claim 2 wherein the dressing further comprises a medical grade adhesive compositions.

5. The method of claim 4 wherein the adhesive composition comprises a polymer, and a water-swellable hydrocolloid.

6. The method of claim 1 wherein the infrared blocking compound is present in an amount sufficient to maintain the temperature of the affected area within 1° C. of the temperature of adjacent healthy skin.

* * * * *